United States Patent [19]
Lui et al.

[11] Patent Number: 5,306,849
[45] Date of Patent: Apr. 26, 1994

[54] PROCESS FOR THE PREPARATION OF HALOGENATED AROMATICS

[75] Inventors: Norbert Lui, Cologna; Dietmar Bielefeldt, Ratingen; Albrecht Marhold, Leverkusen, all of Fed. Rep. of Germany

[73] Assignee: Bayer Aktiengesellschaft, Leverkusen, Fed. Rep. of Germany

[21] Appl. No.: 98,689

[22] Filed: Jul. 28, 1993

[30] Foreign Application Priority Data

Aug. 4, 1992 [DE] Fed. Rep. of Germany ....... 4225763

[51] Int. Cl.$^5$ .............................................. C07C 17/33
[52] U.S. Cl. .................................... 570/173; 570/123; 570/124; 570/127; 570/143; 570/164; 570/165; 570/190; 570/201
[58] Field of Search ............... 570/127, 143, 164, 165, 570/173, 123, 190, 201

[56] References Cited

U.S. PATENT DOCUMENTS

| | | | |
|---|---|---|---|
| 4,622,431 | 11/1986 | Briody et al. | 570/201 |
| 4,656,311 | 4/1987 | Desbois | 568/775 |
| 4,814,524 | 3/1989 | Briody et al. | 570/201 |

FOREIGN PATENT DOCUMENTS

| | | |
|---|---|---|
| 717112 | 8/1965 | Canada ........................ 570/201 |
| 0213047 | 3/1987 | European Pat. Off. . |
| 0427603 | 11/1990 | European Pat. Off. . |

*Primary Examiner*—Werren B. Lone
*Attorney, Agent, or Firm*—Sprung Horn Kramer & Woods

[57] ABSTRACT

Halogenated aromatics are prepared by heating halogenoformic acid esters to 80° to 280° C. in the presence of hydrogen fluoride or a catalytic amount of one or more Lewis acids from the group comprising aluminium halides, iron halides and antimony halides, and in the liquid phase.

13 Claims, No Drawings

PROCESS FOR THE PREPARATION OF HALOGENATED AROMATICS

The present invention relates to a liquid phase process for the preparation of fluorinated and/or chlorinated aromatics from aromatic fluoro- or chloro-formic acid esters.

It is known that aliphatic fluoro- and chloro-formic acid esters can be converted thermally to the corresponding fluoro- and chloro-alkanes in the liquid phase in the presence of Lewis acids (see German Offenlegungsschrift 2 931 777, U.S. Pat. No. 4,814,524 and German Patent Specification 857 350).

Attempts to apply this reaction to aromatic halogenoformic acid esters have shown that aromatic halogenoformic acid esters react in a different way from aliphatic halogenoformic acid esters. On heating in the presence of aromatics and Lewis acids, aromatic, chloroformic acid esters do not react to give chlorinated aromatics with concomitant decarboxylation, but undergo a Friedel-Crafts reaction to give phenyl benzoates (J. Org. Chem. 22, 325 (1957)). Even if the reaction is carried out in the absence of aromatic solvents, it is therefore to be expected that any chlorobenzene produced by decarboxylation will react immediately with aromatic chloroformic acid ester still present to give phenyl benzoates, and that chlorobenzene will not be able to be isolated.

To prepare fluorinated aromatics, it has been proposed to react 1 mol of aromatic halogenoformic acid ester in the presence of 50 mol of hydrogen fluoride and 3 mol of trifluoromethanesulphonic acid in the liquid phase. Apart from using two different auxiliary substances, this process has the disadvantage that fluorinated aromatics are only obtained in yields of 1 to 14%.

Other processes for the preparation of substituted halogenated aromatics also have disadvantages. Thus the direct halogenation of alkylated aromatics gives mixtures of isomers which cannot easily be separated and which often contain only a small proportion of the desired isomer (J. Org. Chem. 55, 5260 to 5269 (1990)).

The blocking of undesired substitution positions with tertiary butyl groups permits the selective introduction of fluorine into aromatic rings by nitration, reduction, diazotisation, boiling in the presence of fluoride ions and elimination of the tertiary butyl groups (J. Chem. Soc. Perkin Trans. I 1987, 1). The disadvantage here is that this is a multi-step procedure.

There is also a multi-step synthesis for the preparation of 2,6-dialkylhalogenobenzenes from 2,3-dimethyl butadiene which involves carrying out reactions with dichlorocarbene and triphenyltin hydride (Synthesis, volume 6–7, pp. 647 to 649). The 2,3-dimethylbutadiene required is not readily accessible and hence is expensive. Here too, the procedure is laborious and of no interest on the industrial scale.

Finally, aromatic halogenoformic acid esters can be converted to halogenated aromatics in the gas phase in the presence of aluminium oxide optionally coated with noble metals (European Patent Applications A-188 241 and A-427 603).

A process for the preparation of halogenated aromatics of formula (I):

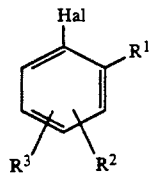

(I)

in which
Hal is fluorine or chlorine,
$R^1$ is $C_1$-$C_6$-alkyl,
$R^2$ is hydrogen or $C_1$-$C_6$-alkyl and
$R^3$ is hydrogen, $C_1$-$C_6$-alkyl, fluorine, chlorine or bromine, has now been found which is characterised in that halogenoformic acid esters of formula (II):

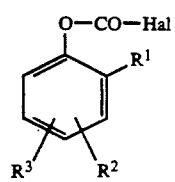

(II)

in which the symbols used are as defined for formula (I), are heated to 80° to 280° C. in the presence of hydrogen fluoride or a catalytic amount of one or more Lewis acids from the group comprising aluminium halides, iron halides and antimony halides, and in the liquid phase.

Preferably, in formulae (I) and (II),
$R^1$ is linear or branched $C_1$-$C_6$-alkyl or cyclic $C_5$-$C_6$-alkyl,
$R^2$ is hydrogen, linear or branched $C_1$-$C_6$-alkyl or cyclic $C_5$-$C_6$-alkyl and
$R^3$ is hydrogen, linear or branched $C_1$-$C_6$-alkyl, cyclic $C_5$-$C_6$-alkyl, fluorine or chlorine.

Particularly preferably,
$R^1$ and $R^2$ independently of one another are methyl, ethyl, n-butyl or i-propyl and
$R^3$ is hydrogen or methyl.

Furthermore, it is preferable if the substituent $R^2$ is not hydrogen and if the substituents $R^1$ and $R^2$ are located in the 2- and 6-positions relative to Hal. Halogenated aromatics of formula (I) are obtained in particularly high yields in these cases.

The process according to the invention is particularly suitable for the use of 2,6-dimethylphenyl halogenoformate, it being preferable to use the chloroformate with Lewis acids to prepare 2,6-dimethylchlorobenzene or with hydrogen fluoride to prepare 2,6-dimethyl fluorobenzene.

The halogenoformic acid esters of formula (II) required as starting compounds for carrying out the process according to the invention are known or can be prepared analogously to known compounds.

If the process according to the invention is carried out with hydrogen fluoride, commercially available anhydrous hydrogen fluoride is particularly suitable for this purpose. Hydrogen fluoride can be used for example in amounts of 1 to 100 mol, preferably 2 to 50 mol, per mole of halogenoformic acid ester of formula (II). When working with hydrogen fluoride, an appropriate pressure has to be applied in order to ensure that at least part of the hydrogen fluoride is still in the liquid phase at the reaction temperature. The procedure with hydrogen fluoride is particularly suitable for the preparation of fluorinated aromatics of formula (I) from fluoro- or chloro-formic acid esters of formula (II).

If the process according to the invention is carried out with Lewis acids from the group comprising aluminium halides, iron halides and antimony halides, suitable examples of the latter are aluminium trichloride, iron trichloride, aluminium oxide pretreated with hydrogen chloride or hydrogen fluoride, and antimony pentafluoride. The conversion of chloroformic acid esters to chlorinated aromatics is advantageously carried out using chloride-containing Lewis acids, especially aluminium trichloride, and the conversion of fluoroformic acid esters to fluorinated aromatics is advantageously carried out using fluoride-containing Lewis acids, especially antimony pentafluoride, or hydrogen fluoride.

Lewis acids, with the exception of hydrogen fluoride, can be used e.g. in amounts of 0.1 to 10 mol %, preferably 1 to 7 mol %, based on the halogenoformic acid ester of formula (II).

When working with Lewis acids, it is often possible to reflux the halogenoformic acid ester of formula (II) used, at normal pressure. It is also possible to work in the presence of solvents, e.g. in the presence of halogenated hydrocarbons, but it is then often necessary to use elevated pressures or closed vessels in order to be able to keep the entire system essentially in the liquid phase at the reaction temperature. When using hydrogen fluoride, it is again possible to work in the presence of solvents, although frequently to no particular advantage because excess hydrogen fluoride can itself act as a solvent.

Preferred reaction temperatures are from 90° to 240° C.

The process according to the invention can be carried out batchwise, for example in reaction vessels for normal pressure or in stirred autoclaves, or else continuously, e.g. in a heatable reaction tube filled with packing, a halogenoformic acid ester of formula (II) and hydrogen fluoride being allowed to trickle down over the packing under pressure. Examples of suitable reactor materials for the process according to the invention are stainless steels.

The reaction according to the invention is generally finished after 1 to 5 hours. The reaction mixture can then be worked up e.g. in the following manner: It is cooled, any remaining pressure is released, any excess hydrogen fluoride present is distilled off, the resulting mixture is discharged onto water or ice and, optionally after the addition of a water-immiscible organic solvent, e.g. methylene chloride, the organic phase is separated off, dried and distilled, optionally under vacuum.

The process according to the invention has a number of advantages. It affords the preparation of halogenated aromatics of formula (I), especially 2,6-dialkyl-chloro- and -fluoro-benzenes, in a simple manner (one step) and in good yields. It can be carried out in simple apparatuses and at relatively low temperatures. Only one auxiliary substance (hydrogen fluoride or a Lewis acid) is required.

It is surprising that, despite the presence of Lewis acids or hydrogen fluoride, Friedel-Crafts reactions do not occur in the process according to the invention, or at most occur to a very minor extent.

Examples

Example 1

0.8 g of anhydrous aluminium chloride was added to 50 g of 2,6-dimethylphenyl chloroformate and the mixture was heated to 200° C. at normal pressure. The evolution of carbon dioxide started above 180° C. and finished after 3.5 hours. The reaction mixture was then cooled, water was added, the organic phase was separated off, the aqueous phase was extracted with methylene chloride, the organic phase which had been separated off was combined with the methylene chloride phase and the combined phases were dried over sodium sulphate and distilled under vacuum. 2,6-Dimethylchlorobenzene was obtained in a yield of 64%.

Example 2

0.3 g of anhydrous aluminium chloride was of 2,6-dimethylphenyl chloroformate and the mixture was heated to 200° C. at normal pressure. A further 150 g of 2,6-dimethylphenyl chloroformate and a further one gram of anhydrous aluminium chloride were then metered in over a period of 2 hours and the 2,6-dimethylchlorobenzene formed was simultaneously distilled off. The reaction did not proceed to completion and a mixture of 2,6-dimethylphenyl chloroformate and 2,6-dimethylchlorobenzene was obtained. Separation by distillation gave a 74% yield of 2,6-dimethylchlorobenzene (based on the conversion).

Example 3

2.1 g of anhydrous aluminium bromide were added to 50 g 2,6-dimethylphenyl chloroformate and the mixture was of heated to 200° C. at normal pressure. When the evolution of carbon dioxide had ended, the reaction mixture was cooled and examined by gas chromatography. It contained 2,6-dimethylchlorobenzene.

Example 4

1.3 g of anhydrous iron(III) chloride were added to 50 g of 2,6-dimethylphenyl chloroformate and the mixture was heated to 200° C. at normal pressure. When the evolution of carbon dioxide had ended, the reaction mixture was worked up as described in Example 1. 2,6-Dimethylchlorobenzene was obtained in a yield of 40%.

Example 5

0.5 g of anhydrous aluminium chloride was added to 50 g of 2,4,6-trimethylphenyl chloroformate and the mixture was heated at 180° C. for 1.5 hours at normal pressure. The reaction mixture was then cooled and worked up as described in Example 1. 2,4,6-Trimethylchlorobenzene was obtained in a yield of 72%.

Example 6

0.4 g of anhydrous aluminium chloride was added to 20 g of 2,3-dimethylphenyl chloroformate and the mixture was heated at 200° C. for 4.5 hours at normal pressure. The reaction mixture was then cooled and worked up as described in Example 1. 2,3-Dimethylchlorobenzene was obtained in a yield of 18%, which is considerable despite the unfavourable substitution pattern.

Example 7

0.5 g of anhydrous aluminium chloride was added to 15 g of 2,4-dimethylphenyl chloroformate and the mixture was heated at 200° C. for 3 hours at normal pressure. The reaction mixture was cooled and worked up as described in Example 1. 2,4-Dimethylchlorobenzene was obtained in a yield of 20%, which is considerable despite the unfavourable substitution pattern.

Example 8

0.35 g of anhydrous aluminium chloride was added to 25 g of 2-isopropylphenyl chloroformate and the mixture was heated at 200° C. for 3 hours at normal pressure. The reaction mixture was cooled and worked up as described in Example 1. 2-Isopropylchlorobenzene was obtained in a yield of 20%, which is considerable despite the unfavourable substitution pattern.

Example 9

2000 ml of anhydrous hydrogen fluoride were placed at 0° in a stainless steel laboratory autoclave and 500 g of 2,6-dimethylphenyl chloroformate were added dropwise. The autoclave was then sealed and heated at a maximum temperature of 130° C. for 3 hours. The pressure of the gases evolved was released at 26 bar. The autoclave was then cooled to room temperature and the excess hydrogen fluoride was distilled off. The remaining reaction mixture was poured onto ice and the organic phase was separated off and distilled under vacuum. 2,6-Dimethylfluorobenzene was obtained in a yield of 69%.

Example 10

1000 ml of anhydrous hydrogen fluoride were placed at 0° C. in a stainless steel laboratory autoclave and 500 g of 2,6-dimethylphenyl chloroformate were added dropwise. The reaction was carried out and the reaction mixture worked up as described in Example 9. 2,6-Dimethylfluorobenzene was obtained in a yield of 51%.

Example 11

500 ml of anhydrous hydrogen fluoride were placed at 0° C. in a stainless steel laboratory autoclave and 1000 g of 2,6-dimethylphenyl chloroformate were added dropwise. The autoclave was then sealed and heated at a maximum temperature of 110° C. for 2 hours, the pressure of the gases formed being released at 30 bar. The reaction mixture was worked up as described in Example 9. Distillation gave 2,6-dimethylfluorobenzene in a yield of 11% and 2,6-dimethylphenyl fluoroformate in a yield of 68%. The latter can be added to a new batch for the preparation of 2,6-dimethylfluorobenzene (see Example 15).

Example 12

500 ml of anhydrous hydrogen fluoride were placed at 0° C. in a stainless steel laboratory autoclave and 150 g of 2,6-dimethylphenyl chloroformate were added dropwise. The autoclave was sealed and heated at a maximum temperature of 140° C. for 1.5 hours, the pressure of the gases formed being released at 26 bar. The reaction mixture was worked up as described in Example 9. 2,6-Dimethylfluorobenzene was obtained in a yield of 68.4%.

Example 13

1.1 kg of anhydrous hydrogen fluoride were placed in a 3 l autoclave and the autoclave was sealed and heated to 130° C. At this temperature, 1 kg of 2,6-dimethylphenyl chloroformate was pumped in over a period of 3 hours, the pressure of the gases formed being released at 40 bar. Finally, the mixture was stirred for 1 hour at 130° C. The reaction mixture was then cooled and excess hydrogen fluoride was distilled off at 100 mbar. Further working-up of the reaction mixture was carried out as described in Example 9. 2,6-Dimethylfluorobenzene was obtained in a yield of 58.3%.

Example 14

70 ml of hydrogen fluoride and 200 ml of 1,1,2-trifluoro-1,2,2-trichloroethane were placed at 0° C. in a stainless steel autoclave and 100 g of 2,6-dimethylphenyl chloroformate were added dropwise. The autoclave was sealed and heated at a maximum temperature of 160° C. for 5 hours, the pressure of the gases formed being released at 30 bar. The reaction mixture was worked up as described in Example 9. 2,6-Dimethylfluorobenzene was obtained in a yield of 30% and 2,6-dimethylphenyl fluoroformate in a yield of 40%. The latter can be added to a new batch for the preparation of 2,6-dimethylfluorobenzene (see Example 15).

Example 15

200 ml of anhydrous hydrogen fluoride were placed at 0° C. in a stainless steel laboratory autoclave and 100 g of 2,6-dimethylphenyl fluoroformate were added dropwise. The autoclave was sealed and heated at a maximum temperature of 140° C. for 1.5 hours. The reaction mixture was worked up as described in Example 9. 2,6-Dimethylfluorobenzene was obtained in a yield of 75%.

Example 16

3.9 g of antimony pentafluoride were added to 100 g of 2,6-dimethylphenyl fluoroformate and the mixture was heated at 200° C. for 5 hours at normal pressure. The reaction mixture was then cooled and worked up as described in Example 1. 2,6-Dimethylfluorobenzene was obtained in a yield of 40%.

Example 17

600 ml of anhydrous hydrogen fluoride were placed at 0° C. in a stainless steel laboratory autoclave and 180 g of 2,3-dimethylphenyl chloroformate were added dropwise. The autoclave was then sealed and heated at a maximum temperature of 140° C. for 4 hours. The reaction mixture was worked up as described in Example 9 to give a mixture of 43% of 2,3-dimethylfluorobenzene, 3.8% of trimethylfluorobenzene and 2.8% of 2,6-dimethylfluorobenzene.

Example 18

600 ml of anhydrous hydrogen fluoride were placed at 0° C. in a stainless steel laboratory autoclave and 150 g of 2,4,6-trimethylphenyl chloroformate were added dropwise. The autoclave was then sealed and heated at a maximum temperature of 110° C. for 3 hours. The reaction mixture was worked up as described in Example 9 to give a mixture of 43% of 2,4,6-trimethylfluorobenzene, 23% of trimethylfluorobenzene (isomer), 15% of tetramethylfluorobenzene and 9.8% of dimethylfluorobenzene.

Example 19

A 0.7 l heatable tubular stainless steel reactor was filled with stainless steel mesh packing having a diameter and height of 6 mm and a mesh density of 3600 meshes/cm$^2$. The reactor was heated so that a temperature of 120° C. was established in the lower third of the reaction space. 18.5 g of 2,6-dimethylphenyl chloroformate and 200 g of anhydrous hydrogen fluoride per hour were fed into the top of this reactor at a pressure of 23 bar and allowed to trickle through the reactor. The pressure was maintained at the lower discharge point of the reactor with the aid of a valve.

The reaction mixture leaving the reactor over a period of 2 hours was trapped in a mixture of 500 g of ice and 200 ml of methylene chloride. The organic phase was then separated off, the aqueous phase was washed with 200 ml of methylene chloride and the methylene chloride phases were combined, freed of any remaining hydrogen fluoride by the addition of sodium fluoride, then dried over sodium sulphate/sodium fluoride and examined by gas chromatography. With 100% conversion, 2,6-dimethylfluorobenzene had been formed with a selectivity of 88%.

What is claimed is:

1. A process for the preparation of halogenated aromatics of formula (I):

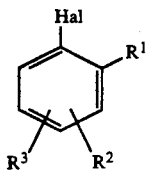
(I)

in which
Hal is fluorine or chlorine,
$R^1$ is $C_1$-$C_6$-alkyl,
$R^2$ is hydrogen or $C_1$-$C_6$-alkyl and
$R^3$ is hydrogen, $C_1$-$C_6$-alkyl, fluorine, chlorine or bromine,
comprising heating in the liquid phase halogenoformic acid esters of formula (II)

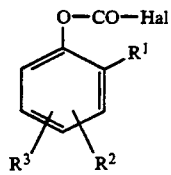
(II)

in which the symbols used are as defined for formula (I), to 80° to 280° C. in the presence of hydrogen fluoride or a catalytic amount of one or more Lewis acids from the group comprising aluminium halides, iron halides and antimony halides.

2. The process of claim 1, in which in formulae (I) and (II),
$R^1$ is linear or branched $C_1$-$C_6$-alkyl or cyclic $C_5$-$C_6$-alkyl,
$R^2$ is hydrogen linear or branched $C_1$-$C_6$-alkyl or cyclic $C_5$-$C_6$-alkyl and
$R^3$ is hydrogen, linear or branched $C_1$-$C_6$-alkyl, cyclic $C_5$-$C_6$-alkyl, fluorine or chlorine.

3. The process of claim 1, in which in formulae (I) and (II) the substituent $R^2$ is not hydrogen and the substituents $R^1$ and $R^2$ are located in the 2- and 6-positions relative to Hal.

4. The process of claim 1, in which 1 to 100 mol of hydrogen fluoride are used per mole of halogenoformic acid ester of formula (II).

5. The process of claim 1, in which 0.1 to 10 mol % of Lewis acids from the group comprising aluminium halides, iron halides and antimony halides are used per mole of halogenoformic acid ester of formula (II).

6. The process of claim 1, in which, when working with Lewis acids, the halogenoformic acid ester of formula (II) used is refluxed, at normal pressure.

7. The process of claim 1, in which the reaction is carried out at 90° to 240° C.

8. The process of claim 1, in which, after the reaction has ended, the reaction mixture is cooled, any remaining pressure is released, any excess hydrogen fluoride present is distilled off, the resulting mixture is discharged onto water or ice and the organic phase is separated off, dried and distilled.

9. The process of claim 8, in which, after discharging the mixture onto water or ice a water-immiscible organic solvent is added.

10. The process of claim 8, in which the final distillation is carried out under vacuum.

11. The process of claim 1, in which 2,6-dimethylphenyl halogenoformate is used.

12. The process of claim 11, in which 2,6-dimethylphenyl chloroformate is used and 2,6-dimethylchlorobenzene is prepared with Lewis acids.

13. The process of claim 11, in which 2,6-dimethylphenyl chloroformate is used and 2,6-dimethylfluorobenzene is prepared with hydrogen fluoride.

* * * * *